United States Patent
Lin et al.

(10) Patent No.: US 7,903,020 B2
(45) Date of Patent: Mar. 8, 2011

(54) SYSTEM AND METHODS FOR REMOTE SENSING USING DOUBLE-SIDEBAND SIGNALS

(75) Inventors: Jenshan Lin, Gainesville, FL (US); Yanming Xiao, San Diego, CA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 548 days.

(21) Appl. No.: 11/911,716

(22) PCT Filed: Mar. 31, 2006

(86) PCT No.: PCT/US2006/012254
§ 371 (c)(1),
(2), (4) Date: Apr. 1, 2008

(87) PCT Pub. No.: WO2006/115704
PCT Pub. Date: Nov. 2, 2006

(65) Prior Publication Data
US 2008/0238757 A1   Oct. 2, 2008

Related U.S. Application Data

(60) Provisional application No. 60/727,529, filed on Oct. 17, 2005, provisional application No. 60/673,902, filed on Apr. 22, 2005.

(51) Int. Cl.
*G01S 13/58* (2006.01)
*A61B 5/02* (2006.01)
(52) U.S. Cl. .......................... 342/22; 600/407
(58) Field of Classification Search .......... 342/22, 342/28, 112, 99; 600/407, 453, 484
See application file for complete search history.

(56) References Cited

U.S. PATENT DOCUMENTS

| | | | |
|---|---|---|---|
| 3,796,208 A | 3/1974 | Bloice | |
| 4,085,740 A | 4/1978 | Allen, Jr. et al. | |
| 4,513,748 A * | 4/1985 | Nowogrodzki et al. | 600/453 |
| 7,272,431 B2 * | 9/2007 | McGrath | 600/509 |

(Continued)

FOREIGN PATENT DOCUMENTS

EP   1058451   12/2000

(Continued)

OTHER PUBLICATIONS

Droitcour et al., Range Correlation and I/Q Performance Benefits in Single-Chip Silicon Doppler Radars for Noncontact Cardiopulmonary Monitoring, IEEE Trans on Microwave Theory & Techniques, Mar. 2004, vol. 52, No. 3.

(Continued)

*Primary Examiner* — Dan Pihulic
(74) *Attorney, Agent, or Firm* — Saliwanchik Lloyd & Eisenschenk

(57) ABSTRACT

A sensing system is provided that includes a transceiver. The transceiver includes a transmitter chain that transmits a double-sideband signal having first and second frequency components, and a receiving chain that receives the double-sideband signal after it is reflected by a target. The system further includes a baseband circuit for extracting information content from the received double-sideband signal. A separation between a first frequency of the first frequency component and a second frequency of the second frequency component causes a spike in a signal response generated by one sideband of the received double-sideband signal to substantially overlap a null point of a signal response generated by the other sideband of the received double-sideband signal.

34 Claims, 11 Drawing Sheets

U.S. PATENT DOCUMENTS

2004/0123667 A1* 7/2004 McGrath .......................... 73/704
2005/0073424 A1   4/2005 Ruoss et al.
2008/0045832 A1* 2/2008 McGrath ....................... 600/427

FOREIGN PATENT DOCUMENTS

GB         2099257         12/1982
WO    WO 2004/013611       2/2004

OTHER PUBLICATIONS

Xiao et al., A Ka-Band Low Power Doppler Radar System for Remote Detection of Cardiopulmonary Motion, Eng. in Medicine & Biol. Soc., 27th Annual Int'l Conf., Shanghai, CN, Sep. 1-4, 2005, pp. 7151-7154.

Stelzer et al., A Microwave Position Sensor with Submillimeter Accuracy, IEEE Trans on Microwave Theory & Techniques, Dec. 1999, vol. 47, No. 12.

Xiao et al., Frequency-tuning Technique for Remote Detection of Heartbeat and Respiration using Low-Power Double-Sideband Transmission in the Ka-Band, IEEE Trans on Microwave Theory & Techniques, May 2006, vol. 54, No. 5.

* cited by examiner

SYSTEM AND METHODS FOR REMOTE SENSING USING DOUBLE-SIDEBAND SIGNALS

CROSS-REFERENCE TO RELATED APPLICATIONS

This application is a §371 national stage entry of International Application No. PCT/US2006/012254, filed Mar. 31, 2006, which claims priority to both U.S. Provisional Application No. 60/727,529, filed Oct. 17, 2005, and U.S. Provisional Application No. 60/673,902, filed Apr. 22, 2005, all of which are hereby incorporated by reference.

FIELD OF THE INVENTION

The present invention is related to the field of signal detection and processing, and more particularly, to detection using double-sideband signals.

BACKGROUND

A Doppler radar motion-sensing system typically transmits a continuous-wave (CW) signal, which is reflected off a target and then demodulated in a receiver. According to Doppler theory, a target characterized by a time varying position, but a net zero velocity, will reflect a transmitted signal after having modulated the phase of the signal proportionately to the position of the time-varying target.

Microwave Doppler radar has been used for wireless sensor applications now for a number of years. Among the more prevalent applications of microwave Doppler radar are weather sensing, position and distance sensing, and automobile speed sensing. More recently, however, microwave Doppler radar has been receiving increased attention as a remote-sensing device for health-related and life-signs monitoring and detection. In the fields of health-care monitoring and life-signs sensing, microwave Doppler radar has been used for sensing physiological phenomena, for sensing signs of life to locate persons trapped in earthquake rubble, and cardiopulmonary monitoring of patients afflicted with sleep apnea syndrome.

For example, consistent with the Doppler theory referred to above, the chest-wall of a person such as a monitored patient can be targeted, and a CW radar-type sensing system will receive reflected from the target a signal similar to a signal transmitted to the target. The phase of the reflected signal, however, will be modulated by the time-varying position of the person's chest-wall. The heartbeat and/or breathing signals of the person can be monitored by phase demodulation, which will thus provide a signal proportional to the chest-wall position and thereby provide information about movement due to the person's heartbeat and respiration.

Detecting and measuring cardiopulmonary activity in a human is called for in a wide variety of situations. Cardiopulmonary measurements are typically necessary in the context of medical diagnosis and treatment of a patient, for example. In many situations, there is a need for on-going monitoring of cardiopulmonary activity. Such is the case, for example, with a seriously or chronically ill patient. Monitoring cardiopulmonary activity is especially important, for example, in the case of patients suffering from heart-related and respiratory disorders, such as sleep apnea syndrome. Monitoring cardiopulmonary activity can also be desirable as part of the care of infants or the elderly.

The use of microwave Doppler radar offers the advantage of remote sensing of cardiopulmonary activity, allowing heartbeat and respiration rates to be monitored without direct patient contact. With microwave Doppler radar, heart and respiration signatures are determined based upon the chest motion of a monitored patient, as described above.

A significant limitation on this use of microwave Doppler radar, however, is that such systems typically employ heavy, bulky, and expensive waveguide components that ordinarily are only practical for specialized applications. One approach for obviating these problems is to combine microwave Doppler radar with radio frequency integrated circuit (RFIC) technology. This combination, however, gives rise to its own set of problems. One problem is that the complementary metal-oxide semiconductor (CMOS) oscillators, which are often employed in such RFIC-based systems, suffer from significantly high phase noise—noise much higher than that of a hybrid oscillator incorporating an off-chip, high-quality inductor.

The high phase noise problem is a significant limitation on CMOS motion-detecting radar systems. Since physiological motion is encoded in a phase modulation of the radio signal, close-in phase noise is a critical parameter. This problem can be dealt with by taking advantage of the range correlation phase noise filter effect so as to mitigate the effects of phase noise.

A remaining problem, though, concerns the frequency range of a RFIC-based microwave Doppler radar system. Conventional CW sensing typically utilizes waves that lie in the low-frequency range of the electromagnetic spectrum. Toward the lower end of the frequency range in which such a system typically operates, there is considerable crowding owing to the many other applications operating at or near such frequencies. For example, the 2.4 GHz ISM band is used for wireless LAN, coreless phones, Bluetooth, and other similar applications. Given the ever increasing number of such applications, it is likely that this problem will only worsen in the future. Thus, the low frequency band tends to be crowded since it is also the band in which many other applications operate. Indeed, many if not most industrial, science, and medical (ISM) equipment are operated at RF frequencies within the 2.4 GHz ISM band, a frequency band in which various types of equipment can be operated without the operators having to acquire a license provided that the devices operated comply with maximum emitted power limits.

Perhaps even more problematic is the fact that the low-frequency electromagnetic waves utilized have relatively long wavelengths, making them less sensitive to small displacements of a monitored target. The lessened accuracy is a particular problem with respect to physiological and patient monitoring in which small movements of, for example, a patient's chest wall are the target of the monitoring device.

Accordingly, there is a need, especially for monitoring cardiopulmonary activity, for a system of remote detection that can operate in a frequency band higher than that of potentially interfering applications. Moreover, there is a need for system that can effectively and efficiently perform remote detection while operating in the higher frequency band.

SUMMARY OF THE INVENTION

The invention is directed to methods and systems using double-sideband signals, such as Ka-band electromagnetic waves, generated by combining two signals of different frequencies such that the separation between the frequencies mitigates or eliminates the severe null-point problem associated with high-frequency sensing signals. The invention enables, for example, the detection of small motions using Ka-band electromagnetic waves having significantly enhanced detection sensitivity.

One embodiment of the invention is a method of remote sensing. The method can include transmitting a double-sided electromagnetic wave comprising a first frequency component and a second frequency component, receiving the electromagnetic wave after it is reflected by a subject. Using the method, a separation between the first and second frequency components can cause a spike in a signal response corresponding to one side band of the double-sided electromagnetic wave to substantially overlap a null point of a signal response corresponding to the other side band of the double-sided electromagnetic wave.

Another embodiment of the invention is a sensing system. The system can include a transceiver having a transmitter chain that transmits a double-sided electromagnetic wave having first and second frequency components, and a receiving chain that receives the double-sided electromagnetic wave after it is reflected by a target. The system can further include a baseband circuit for extracting information content from the double-sided electromagnetic wave. Moreover, the system can provide a separation between the first and second frequency components such that a spike in a signal response generated by one sideband of the double-sided electromagnetic wave substantially overlaps a null point of a signal response generated by the other sideband of the double-sided electromagnetic wave.

Still another embodiment of the is a system for sensing cardiopulmonary activity. The system can include a Ka-band transceiver for transmitting a sensing signal to a monitored subject and receiving a modulated signal from the monitored subject. The sensing signal, more particularly, can have a frequency within a Ka-band range of frequencies, and the modulated signal can be modulated based upon cardiopulmonary activity in the monitored subject. The system further can include a baseband circuit connected to the Ka-band transceiver for generating a baseband signal output that is based upon the modulated signal and that is indicative of the cardiopulmonary activity in the monitored subject.

Another embodiment of the invention is a machine-readable storage medium for storing machine-directing instructions. The stored instructions can effect a transmitting of a double-sided electromagnetic wave comprising a first frequency component and a second frequency component and a receiving of the electromagnetic wave after it is reflected by a subject. A separation between the first and second frequency components can cause a spike in a signal response corresponding to one side band of the double-sided electromagnetic wave to substantially overlap a null point of a signal response corresponding to the other side band of the double-sided electromagnetic wave.

BRIEF DESCRIPTION OF THE DRAWINGS

There are shown in the drawings, embodiments which are presently preferred, it being understood, however, that the invention is not limited to the precise arrangements and instrumentalities shown.

DETAILED DESCRIPTION OF THE INVENTION

Figure 1:
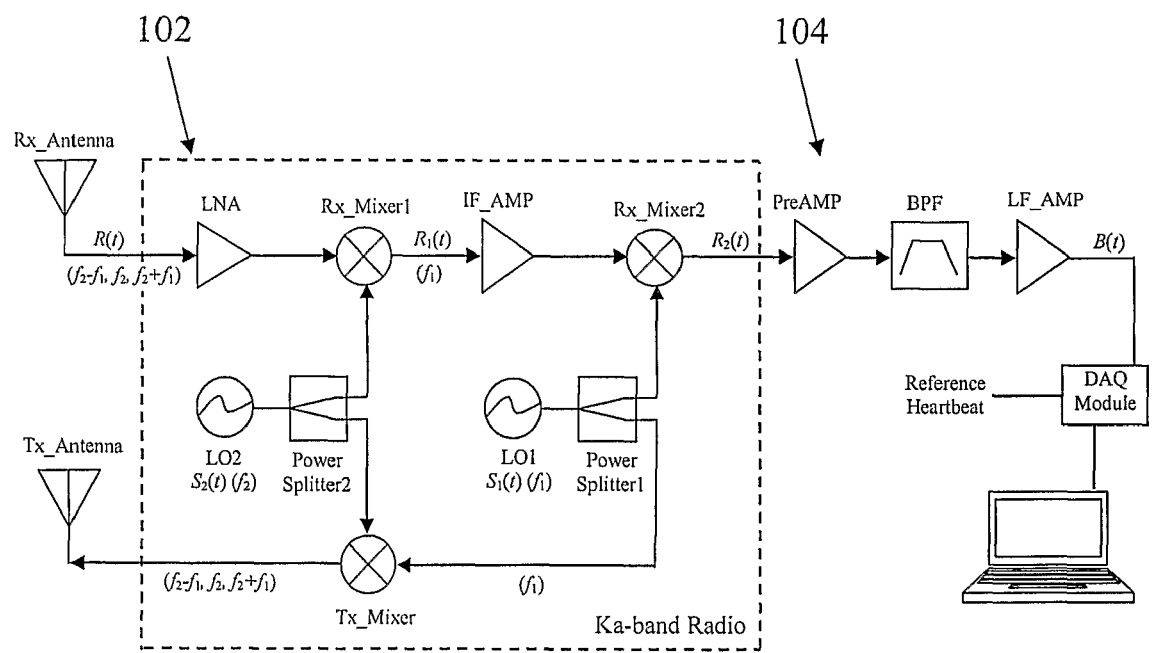
FIG. 1 is a schematic diagram of a system for remote sensing of cardiopulmonary activity, according to one embodiment of the present invention.

A system 100 for remote sensing, according to one embodiment of the present invention, is schematically illustrated in FIG. 1. The system 100 illustratively includes a transceiver, such as a Ka-band transceiver 102, and a baseband circuit 104 electrically coupled to the transceiver. As explained herein, the Ka-band transceiver transmits a sensing signal to a monitored subject (not shown) such as medical patient or infant, and receives a modulated signal from the monitored subject. The sensing signal, more particularly, has a frequency that can be within the Ka-band range of frequencies. The modulated signal is modulated based upon the cardiopulmonary activity in the monitored subject.

The Ka-band transceiver 102, more particularly, can comprise a receiver chain and a transmitter chain. As illustrated, the receiver chain can include a receiving antenna (Rx_Antenna), a low noise amplifier (LNA), two down-converters (Rx_Mixer1 and Rx_Mixer2), and an IF amplifier (IF_AMP). The transmitter chain can comprise a transmitting antenna Tx_Antenna and one up-converter (Tx_Mixer1). The baseband circuit 104 illustrative comprises a preamplifier (PreAMP), a band pass filter (BPF), and a low frequency amplifier (LF_AMP).

Note that as illustrated, the Ka-band transceiver 102 further includes two power splitters. The respective power splitters, more particularly, can each be 3-dB power splitters. The power splitters divide the power of an intermediate frequency (IF) carrier signal into two components, $S_1(t)$ and $S_2(t)$. Half of the power from each power splitter is fed to the transmitter chain, and the other half is supplied to the receiver chain. Note further, that the input of Tx_Mixer1, the up-converter, is terminated with a 50-.OMEGA. resistor. This unique arrangement of components can convert a general-purpose Ka-band transceiver so that it functions as a Doppler radar sensor.

As will be readily understood by one of ordinary skill in the art, the Ka-band transceiver 102, as described, is an indirect-conversion transceiver that employs a two-step conversion to mitigate the severe DC offset problem that otherwise occurs normally with direct-conversion receivers. This unique advantage is achieved because the mixer and LO at the last stage of the indirect receiver operate at low frequency. This reduces the DC offset and the associated 1/f noise at baseband. The RF and IF frequencies can be tuned so as to avoid "null" points in the measurement.

The transmitting and receiving antennas can both be 4×4 printed patch antenna arrays fabricated on Rogers RO3003 PTFE/Ceramic laminates with dielectric constant $\in_r=3.0$ and a substrate thickness of 0.5-mm. Each can have a maximum antenna gain of 12.9-dB at 28-GHz, and an estimated beamwidth of 10°×10°. Compared to a single patch antenna, the antenna array has higher directivity gain. This increases the detection distance of the system 100 and reduces interference from other directions. The baseband circuits can implemented, for example, using LM324 low power op-amp. The bandpass filter BPF can pass signal frequency can extend from 0.1-Hz to 10-Hz. The preamplifier PreAMP, which can have the same frequency as the low frequency amplifier LF_AMP, can have a variable gain from 20-dB to 40-dB.

When the same LO source is used for the transmitter and the receiver, the range correlation effect greatly decreases the noise spectrum at baseband. For this reason, a voltage controlled oscillator (VCO) can be used as the LO in the Ka-hand Doppler radar despite VCO high phase noise.

One aspect of the invention is the use of double-sideband electromagnetic waves, such as Ka-band electromagnetic waves, for detecting small motions of a target. Utilization of Ka-band electromagnetic waves provides significantly enhanced detection sensitivity, but can also give rise to a severe null-point problem. Another aspect of the invention, however, overcomes the null-point problem. More particularly, as described herein, the invention utilizes double-sideband Ka-band electromagnetic waves that are generated, according to the invention, by combining two signals of different frequencies such that the separation between the frequencies mitigates or eliminates the null-point problem.

The enhanced detection sensitivity achieved with the invention allows for small motion detections not otherwise feasible. The invention enables the detection, for example, of heartbeat-induced and/or respiration-induced changes in the chest-wall of a monitored patient using electromagnetic waves in the Ka-band frequency range. Other applications of the invention include physical-reaction sensing in connection with lie detection, other types of biomedical sensing, and radar sensing, such as radar used by individual combat soldiers for "behind-the-wall" sensing.

Referring still to FIG. 1, in effecting a two-step signal conversion according to the invention, the first low oscillator (LO1) generates a signal $S_1(t)$, having a frequency $f_1$. The second low oscillator (LO2) generates a signal $S_2(t)$, having a frequency $f_2$. As will be readily understood by one of ordinary skill in the art, the power of $S_1(t)$ and $S_2(t)$ can be split by the two power splitters, such as the 3 dB power splitters shown. Half of the power is sent to the transmitter chain, and the other half is sent to the receiver chain.

The output T(t) of the up-converter (Tx_Mixer) is not filtered. Accordingly, the output has two main frequency components: a lower sideband $f_L=f_2-f_1$ and an upper sideband $f_U=f_2+f_1$. There typically is one more frequency component $f_2$ in the output of up-converter (Tx_Mixer) that results from the LO leakage from the second low oscillator (LO2).

Figure 2:
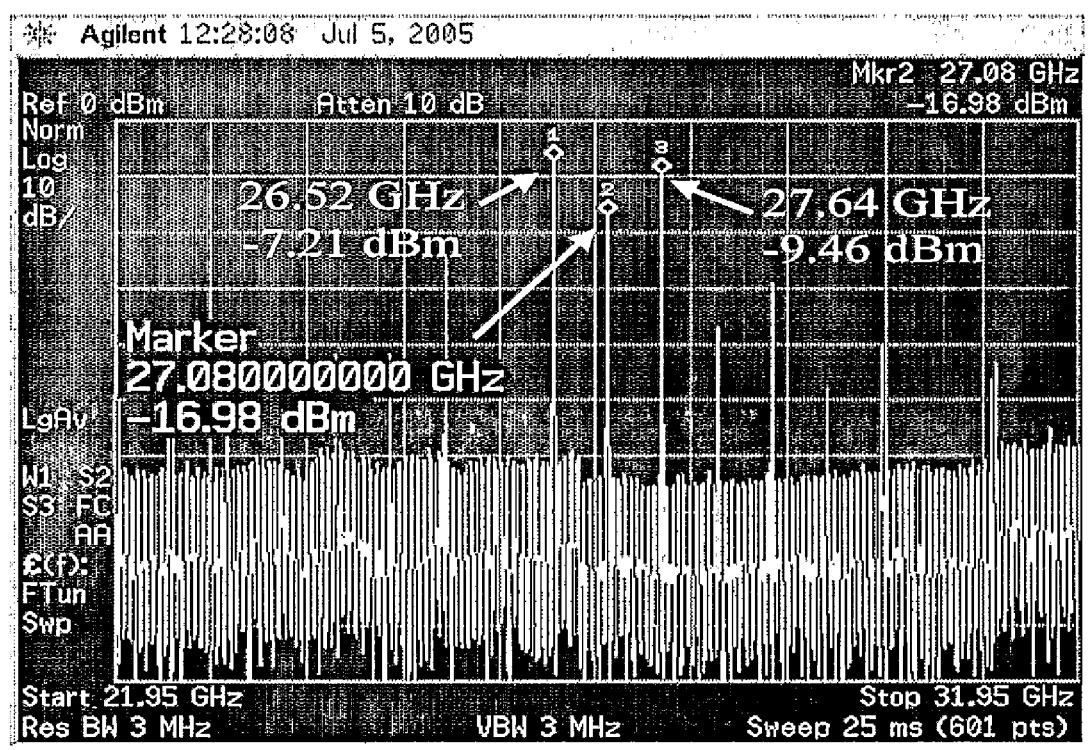
FIG. 2 is an exemplary display of an output spectrum generated with the detecting system illustrated in FIG. 1.

Referring additionally to FIG. 2, an output power spectrum of the transmitter measured at the transmitting antenna (TX_Antenna) connector is shown. With respect to this particular embodiment, the lower sideband and upper sideband frequencies are 26.52 GHz and 27.64 GHz, respectively, with power levels of −7.21 0dBm and −9.64 dBm, respectively. The 27.08 GHz frequency in between is the LO leakage from the second low oscillator (LO2) due to non-ideal isolation of the up-converter (Tx_Mixer). Although the LO leakage is evident, it does not affect the baseband signal detection, as explained herein.

In the receiver chain of the Ka-band transceiver 102, the received signal R(t) is the reflected wave from a target such as a subject whose heartbeat and/or respiration are detected and monitored using the system 100. The received signal R(t) is correlated to the transmitted signal T(t), but with the former signal's phase modulated by the time-varying position of the target, such as a monitored patient's chest-wall. After the first down-conversion by the first down-converter (Rx_Mixer1), the received signal $R_1(t)$ consists of two modulated signals at frequency $f_1$, the signals down-converted from the lower sideband $f_L=f_2-f_1$ and upper sideband $f_U=f_2+f_1$, respectively.

Chest-wall position information, for example, is modulated on the phases of these two signals at frequency $f_1$. In addition, the received signal $R_1(t)$ also has a DC offset and a baseband signal carrying chest-wall motion information, the former due to self-mixing of the LO2 leakage transmission and the latter down-converted from the $f_2$ component in the received signal R(t).

If a direct down-conversion is effected, the DC offset could introduce severe problems, such as saturating the baseband circuitry. In the meantime, reducing DC offset by lowering, or reducing, LO leakage through isolation is difficult to achieve in higher frequency mixers, resulting in a large DC offset. Thus, according to the invention, an indirect conversion receiver architecture is utilized. The large DC offset and the near DC signals are removed by the bandpass frequency response of the IF amplifier (IF_AMP). Therefore, in the following description, the $f_2$ frequency component in the transmitted wave can be ignored because it does not affect the baseband signal. After the second down-conversion by the second down-converter (Rx_Mixer2), the output $R_2(t)$ consists of a baseband signal carrying the subject's chest-motion information and unwanted high frequency spurs that are filtered out in the bandpass circuit 104.

According to another embodiment of the invention, two types of low-profile printed patch antenna specifically designed and fabricated are used. One is a printed single patch antenna fabricated on a high frequency substrate material, GML1000, with dielectric constant $\in_r$ of 3.2 and substrate thickness of 0.762 mm. This antenna achieves a maximum antenna gain of 3.9 dB at 30 GHz and an estimated beamwidth of 60°×80°.

The other antenna is a 4×4 printed patch antenna array fabricated on Rogers RO3003 PTFE/Ceramic laminates with a dielectric constant $\in_r$ of 3.0 and a substrate thickness of 0.508 mm. The total size is 20.9×28.2 mm². The antenna array, according to this embodiment, achieves a maximum antenna gain of 12.9 dB at 28 GHz and an estimated beamwidtlh of 10°×10°. Other types of antennas can also be used in transmitting and receiving Ka-band signals, these antennas being fabricated on one common substrate. Compared to the single patch antenna, the antenna array has higher directivity gain, and therefore increases the detection distance and reduces interference from other radio devices at other directions.

According to yet another embodiment of the system 100, the baseband circuit 104 comprises two LM324 low power operational amplifiers. The bandpass filter (BPF) has a passband of 0.1-Hz to 10-Hz. The preamplifier (PreAMP) and the low frequency amplifier (LF_AMP), according to this embodiment, both have a variable gain from 20-dB to 40 dB. During the measurement phase, a 22-bit USB data acquisition module, such as the IOtech Personal Daq/54 (DAQ module) can be used to sample the baseband signal. Machine-readable code, such as a LabVIEW program, can be used to process the sampled data and further filter out unwanted spurious responses due to random motion of the monitored subject.

It is useful at this juncture to briefly describe certain theoretical underpinnings of the invention. Since only phase modulation is considered, amplitude variations can be neglected without loss of generality. Accordingly, the two LO signals $S_1(t)$ and $S_2(t)$ generated respectively by the first low oscillator (LO1) and second low oscillator (LO2), respectively, can be written as $$S_1(t) = \cos(2\pi f_1 t + \phi_1(t)), \text{ and} \quad (1)$$

$$S_2(t) = \cos(2\pi f_2 t + \phi_2(t)), \quad (2)$$

where $f_1$ and $f_2$ are the frequencies of $S_1(t)$ and $S_2(t)$, respectively, t is elapsed time, and $\phi_1(t)$ and $\phi_2(t)$ are the phase noises of $S_1(t)$ and $S_2(t)$, respectively.

If the transmitted signal T(t) has only a single frequency component (single sideband) f, then $$T(t) = \cos[2\pi f t + \phi(t)], \quad (3)$$

where $\phi(t)$ is the total phase noise from the signal sources and mixer in the transmitter chain.

Figure 3:
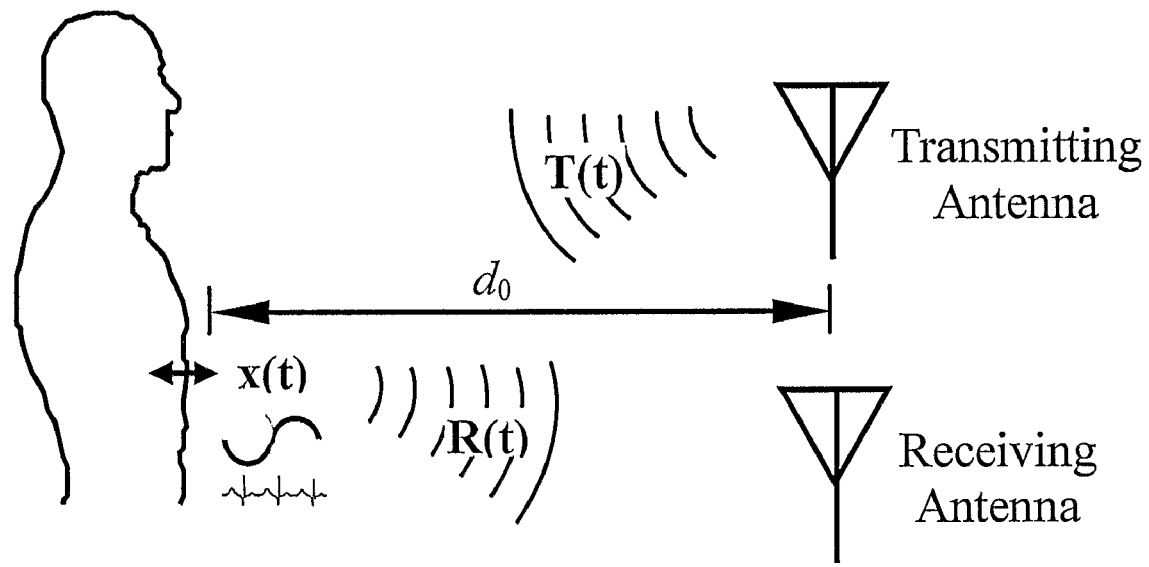
FIG. 3 is a schematic diagram of the operative aspects of the detecting system illustrated in FIG. 1.

When the signal T(t) is reflected back by a target (e.g., a patient's chest-wall) at a distance $d_0$ with a time-varying movement given by x(t), the total distance traveled between the transmitter and receiver is $2d(t) = 2d_0 + 2x(t)$. The operative effects are schematically illustrated in the context of detecting a subject's heartbeat and/or respiration in FIG. 3. The received signal can be approximated as $$R(t) \approx \cos\left[2\pi f t - \frac{4\pi d_0}{\lambda} - \frac{4\pi x(t)}{\lambda} + \phi\left(t - \frac{2d_0}{c}\right)\right], \quad (4)$$

where c is the signal's propagation velocity, $\lambda$ is wavelength in air, which equals to c/f.

The received signal is similar to the transmitted signal, but has a time delay determined by the distance of the target and a phase modulation due to the periodic motion of the target. The information about the periodic motion of the target (e.g., subject's chest wall) can be demodulated if this signal is mixed by an LO signal that is derived from the same sources as the transmitted signal. This radar topology takes advantage of the ability to use the same oscillator for the transmitter and receiver, which keeps the phase noise of the two signals correlated.

The resulting baseband signal B(t) after two-step down-conversion is approximated as $$B(t) = \cos\left[\frac{4\pi d_0}{\lambda} + \theta_0 + \frac{4\pi x(t)}{\lambda} + \Delta\phi(t)\right], \quad (5)$$

where $4\pi d_0/\lambda$ is the constant phase shift due to the distance to the target $d_0$, and $\theta_0$ is the fixed phase shift due to the reflection at surface and the delays between the radio blocks. The term $\Delta\phi(t)$ is the total residual phase noise, which is typically quite small in the baseband due to range correlation effect. A periodic heartbeat and/or breathing signal, for example, can be extracted from B(t) because B(t) is a function of x(t).

From equation (5), the modulated phase $4\pi x(t)/\lambda$ in the baseband output is inversely proportional to the wavelength. For the same displacement, the shorter wavelength provided by the system 100 generates a larger phase modulation. The Ka-band spectrum can span from 26 GHz to 40 GHz, corresponding to wavelengths from 11.5 mm to 7.5 mm. Therefore, the phase generated by a 30 GHz ($\lambda$=10 mm) wave, for example, is 12.5 times (about 22 dB) larger than that at 2.4 GHz ($\lambda$=125 mm). The shorter wavelength is more sensitive to small displacement. This is a decided benefit of using the Ka-band wave provided by the system 100.

Figure 4A:
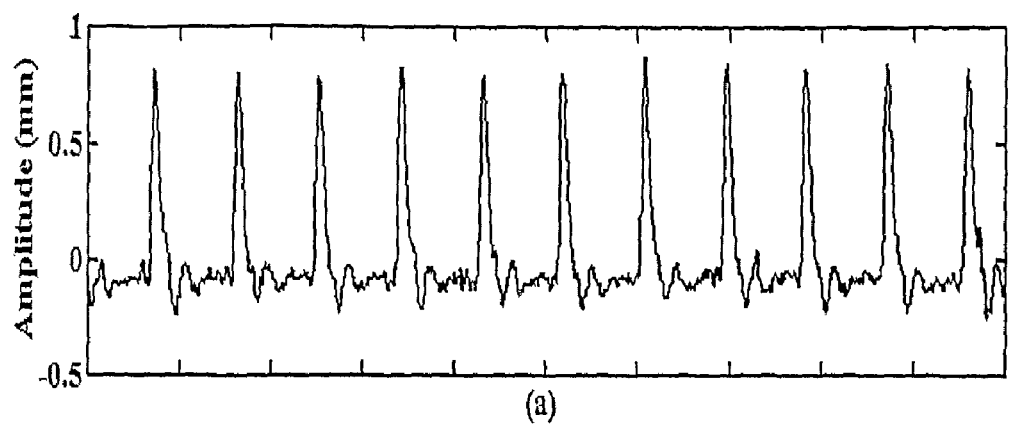
FIGS. 4A and B are exemplary amplitude-versus-time plots of a modeled heartbeat signal and simulated baseband signal, respectively, that simulates the operation of a detecting system according to another embodiment of the invention.
Figure 4B:
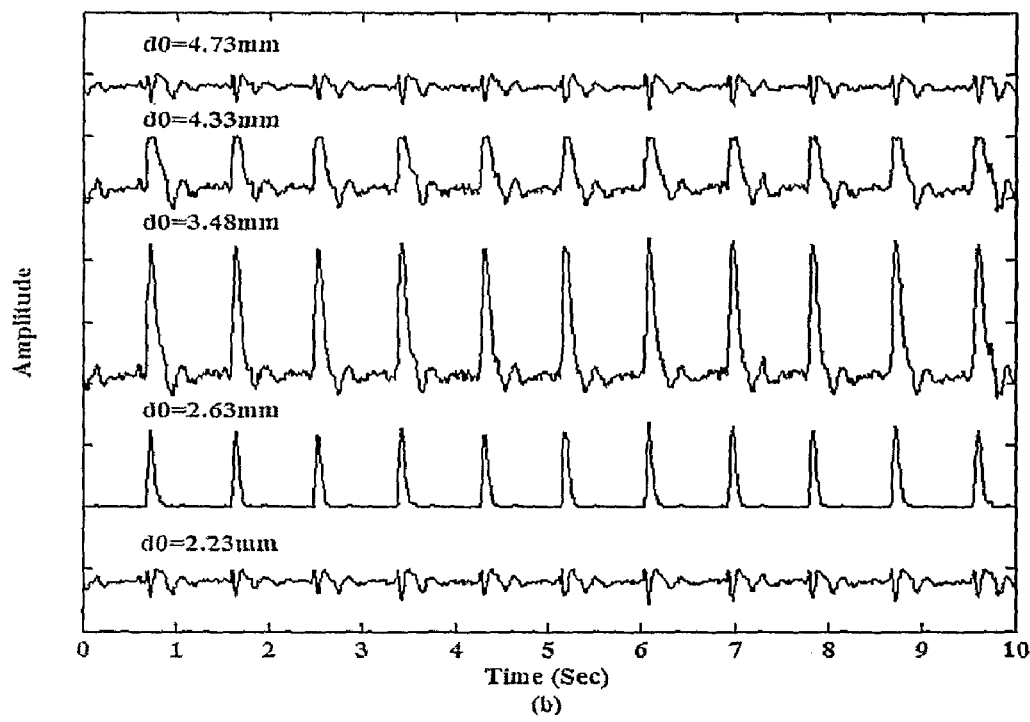

The above-described theoretical aspects of the invention can be modeled and simulated with respect to detecting or monitoring, for example, a subject's heartbeat and/or respiration by assuming that the subject's chest-wall motion amplitude due to heartbeat is 1 mm and that its waveform, as illustrated in FIG. 4A, is modified from the reference heartbeat signal of a finger-tip sensor. Ignoring $\Delta\phi(t)$ and making $\theta_0$ a constant, the baseband signal B(t) varies with the distance $d_0$ when the wavelength $\lambda$ is equal to 10 mm (30 GHz), as illustrated in FIG. 4B. As shown in FIG. 4B, the B(t) amplitude changes periodically from a maximum to a minimum. When the amplitude of B(t) reaches the minimum at $d_0$=2.23 mm, retrieval of the heartbeat signal can be difficult owing to the fact that the signal is all but buried in noise. The distance at which the amplitude of B(t) is a minimum is referred to herein as the null point. In general, when the sensing system and target are separated by a distance that gives rise to a null point when taking a sensing measurement, the detection sensitivity is at its lowest and, accordingly, the sensor has its lowest detection accuracy.

In the converse situation, when the amplitude of B(t) achieves the maximum at $d_0$=3.48 mm, it is considerably less difficult to detect the accurate heartbeat rate because the corresponding rate profile has the same shape as the original signal shown in FIG. 4A. The distance separating a radar system and target that results in the amplitude of B(t) being a maximum is referred to herein as the optimum point. This provides measurements having greatly enhanced detection sensitivity and detection accuracy.

Figure 5:
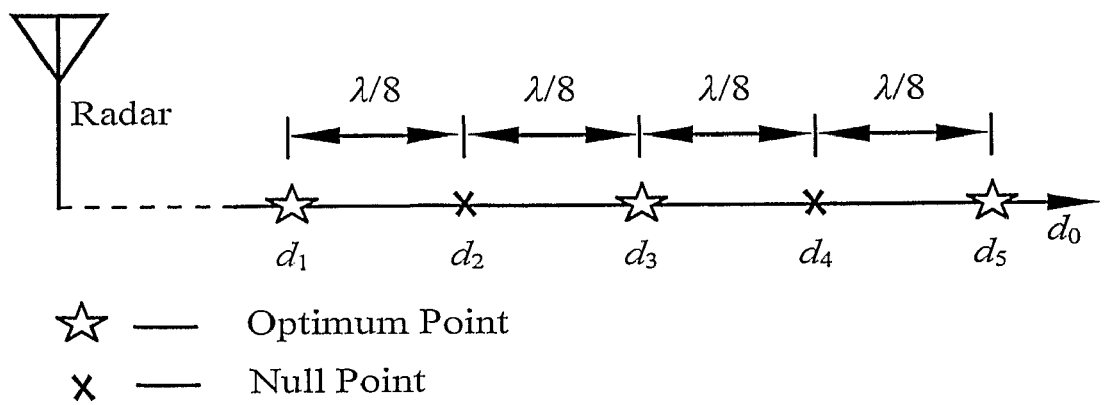
FIG. 5 is schematic diagram of the distances between each of a series of optimum and null points.

FIG. 5 shows the distribution of null points and optimum points along the distance from a radar system to the subject for a single sideband transmitted wave. For a 30 GHz wave, the distance between the adjacent null point and optimum point is only 1.25 mm ($\lambda$/8), which is of the order of chest-wall motion. This distance is typically too small to readily obtain a sufficiently useable measurement.

If the sensing system transmits a single-tone Ka-band wave, the detection accuracy varies dramatically with even a very small movement of the subject, making it extremely difficult to achieve a desirable detection accuracy under this condition. Therefore, a radar system does not perform adequately at higher frequency if it transmits only a single-tone wave.

The null-point problem is solved, according to the invention, by taking the advantage of double sideband waves. The system 100 utilizes a Ka-band wave having two Ka-band frequency components $f_L$, and $f_U$ as the transmitted signal T(t). Therefore, the received signal R(t) has these two frequency components $f_L$ and $f_U$ as well. In the following, $B_L(t)$ and $B_U(t)$ represent the baseband signal components delivered from the $f_L$ and $f_U$ frequency components, respectively. Accordingly, the following equations obtain:

$$B(t) = B_L(t) + B_U(t), \quad (6)$$

$$B_L(t) = \cos\left[\theta_L + \frac{4\pi x(t)}{\lambda_L} + \Delta\phi_L(t)\right], \quad (7)$$

$$B_U(t) = \cos\left[\theta_U + \frac{4\pi x(t)}{\lambda_U} + \Delta\phi_U(t)\right], \quad (8)$$

and $$\theta_L = \frac{4\pi d_0}{\lambda_L} + \theta_{0L}, \quad \theta_U = \frac{4\pi d_0}{\lambda_U} + \theta_{0U}, \quad (9)$$

where $\lambda_L$ and $\lambda_U$ are the wavelengths of the lower sideband and the upper sidebands, respectively. The wavelengths $\lambda_L$ and $\lambda_U$ equal $c/f_L$ and $c/f_U$, respectively. The terms $\theta_L$ and $\theta_U$ are phase shifts that decide the position and distance of the null point, as discussed above.

Figure 6:
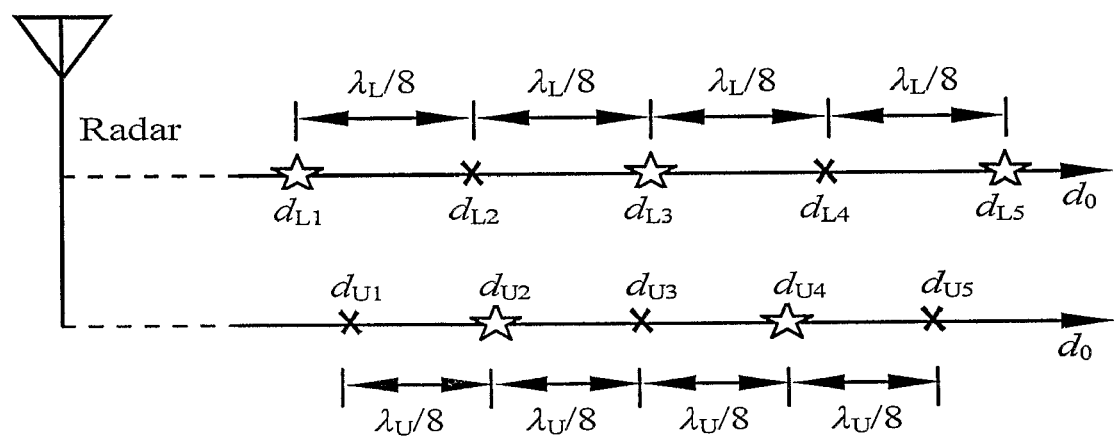
FIG. 6 is schematic diagram of the distances between each of a series of optimum and null points.

From the above discussions, either $B_L(t)$ or $B_U(t)$ has the severe null-point problem and is unable to provide reliable detection. However, when $B_L(t)$ and $B_U(t)$ exist simultaneously, $B(t)$ is the superposition of $B_L(t)$ and $B_U(t)$. $B_L(t)$ and $B_U(t)$ are similar but with a phase difference between them. When, according to the invention, phase difference is appropriately tuned, the baseband output $B(t)$ exhibits much less of a null-point problem than either $B_L(t)$ or $B_U(t)$ alone. Referring additionally now to FIG. 6, the distribution of null points and optimum points for double sideband waves are schematically illustrated. If the LO1 frequency $f_1$ is appropriately tuned, the null points from lower sideband and optimum points from upper sideband, or vice versa, overlap each other.

Note that when the null points from one sideband overlap the optimum points from the other sideband, detection accuracy is significantly enhanced. That is, detection accuracy is significantly enhanced when the null points from the lower sideband and the optimum points from the upper sideband overlap. So, too, if the optimum points from the lower sideband overlap the null points from the upper sideband, detection accuracy is significantly enhanced.

The residual noises $\Delta\phi_L(t)$ and $\Delta\phi_U(t)$ in equations (7) and (8), respectively, are much smaller compared to $\theta$ and to the phase modulation $4\pi x(t)/\lambda$, due to the effect of range correlation. Their effect, therefore, is ignored in the following discussion without any loss of generality. Phase modulations $4\pi x(t)/\lambda_L$ and $4\pi x(t)/\lambda_U$ have nearly equal amplitudes because $\lambda_L$ is very close to $\lambda_U$.

When $\theta_L$ and $\theta_U$ are separated by an even multiple of $\pi$, $B_L(t)$ and $B_U(t)$ are in-phase and synchronized. Therefore, $B(t)$ will give almost the same optimum points and null points at the same places as those given by either $B_L(t)$ or $B_U(t)$ alone, and has the same problem of closely spaced null points that degrade the detection accuracy.

When $\theta_L$ and $\theta_U$ are separated by an odd multiple of $\pi$, $B_L(t)$ and $B_U(t)$ are out of phase. Since $B_L(t)$ and $B_U(t)$ have almost the same amplitudes but with opposite phase, they cancel each other. Therefore, the amplitude of $B(t)$ is quite small and difficult to detect.

As a result, when the phase difference between $\theta_L$ and $\theta_U$ is the integer of $\pi$, a new null-point condition occurs in the measurement. If the null point of the single sideband wave is defined as the local null point, then this new null point condition is defined as a global null point. At this global null point, detection accuracy is at its lowest. The phase difference is $$\theta_U - \theta_L = \frac{4\pi d_0}{\lambda_U} - \frac{4\pi d_0}{\lambda_L} + \Delta\theta_0 = k\pi, \; k = 0, \pm 1, \pm 2, \ldots, \quad (10)$$

where $$\Delta\theta_0 = \theta_{0U} - \theta_{0L}. \quad (11)$$

Substituting $\lambda_L = c/f_L$, $\lambda_U = c/f_U$, yields the following $$f_U - f_L = \frac{c}{4\pi d_0}(k\pi - \Delta\theta_0), \; k = 0, \pm 1, \pm 2, \ldots. \quad (12)$$

Substituting $f_U = f_2 + f_1$, and $f_L = f_2 - f_1$ in equation (12), then yields $$f_1 = \frac{k}{d_0} \cdot 37.5 \text{ MHz} - \frac{c}{8\pi d_0} \cdot \Delta\theta_0, \; k = 0, \pm 1, \pm 2, \ldots, \quad (13)$$

where $d_0$ is the distance.

When $\theta_L$ and $\theta_U$ are separated by an odd multiple of $\pi/2$, $B_L(t)$ and $B_U(t)$ are in quadrature. At least one of $B_L(t)$ and $B_U(t)$ is not at the null point. The one that is not at the null point will determine the final output $B(t)$. Therefore, in this case, the overall detection accuracy will be high. This point is defined as the global optimum point.

Accordingly, the difference between $\theta_U$ and $\theta_L$ is $$\theta_U - \theta_L = \frac{4\pi d_0}{\lambda_U} - \frac{4\pi d_0}{\lambda_L} + \Delta\theta_0 = k\pi, \; k = 0, \pm 1, \pm 2, \ldots \quad (14)$$

Repeating the process described by equations (10)-(13), above, yields $$f_1 = \frac{2k+1}{d_0} 18.75 \text{ MHz} - \frac{c}{8\pi d_0}\Delta\theta_0, \; k = \pm 1, \pm 2, \ldots \quad (15)$$

The above analysis shows that when the position of the subject is fixed, this position can be set to a global optimum point or a global null point by properly choosing the $f_1$ frequency. For example, if at an $f_1$ frequency, the subject position at $d_0 = 1$ m happens to be a null point, this null point can be changed to an optimum point if $f_1$ is tuned to $f_1 \pm (2k+1) \times 18.75$ MHz according to equations (13) and (15). Accordingly, an accurate detection can always be made at an optimum point by adjusting $f_1$ frequency without moving the subject's position.

Figure 7:
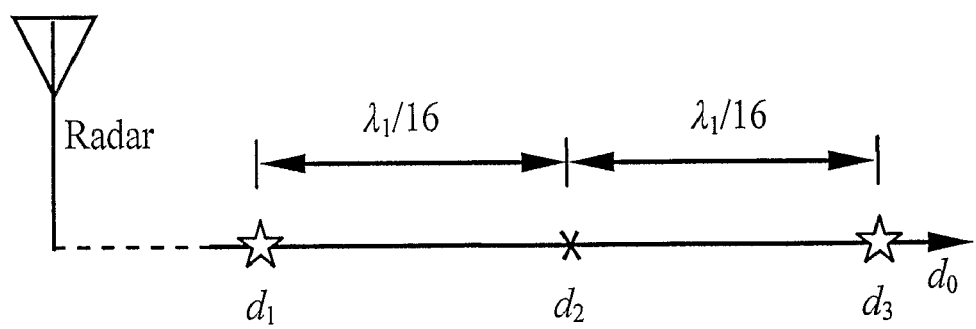
FIG. 7 is schematic diagram of the distances between each of a series of optimum and null points.

When the $f_1$ frequency is fixed, the distribution of the global null points and optimum points for double sideband waves is different from the single baseband case due to the superposition of two baseband signal components. Equations (13) and (15) can be rewritten as $$d_0 = \frac{k}{8}\lambda_1 - \frac{\lambda_1}{8\pi} \cdot \Delta\theta_0, \; k = 0, \pm 1, \pm 2, \ldots \quad (16)$$

and $$d_0 = \frac{(2k+1)}{16} \cdot \lambda_1 - \frac{\lambda_1}{8\pi} \cdot \Delta\theta_0, \; k = 0, \pm 1, \pm 2, \ldots, \quad (17)$$

respectively. From equations (16) and (17), the null points are encountered every $\lambda_1/8$, so, too, are the optimum points. Furthermore, the adjacent null point and optimum point are separated by $\lambda_1/16$. The distribution of null points and optimum points for double sideband waves is shown in FIG. 7.

Ordinarily, the frequency $f_1$ is much lower than frequency $f_2$, so the distance between the adjacent global null point and global optimum point is much longer. For $f_1 = 500$ MHz, which is much smaller than Ka-band frequency, the null point occurs every 75 mm, which is much longer than 2.5 mm for a single 30 GHz wave, so it is possible to obtain a reliable detection accuracy and avoid the null point by adjusting the position of the radar.

Figure 8A:
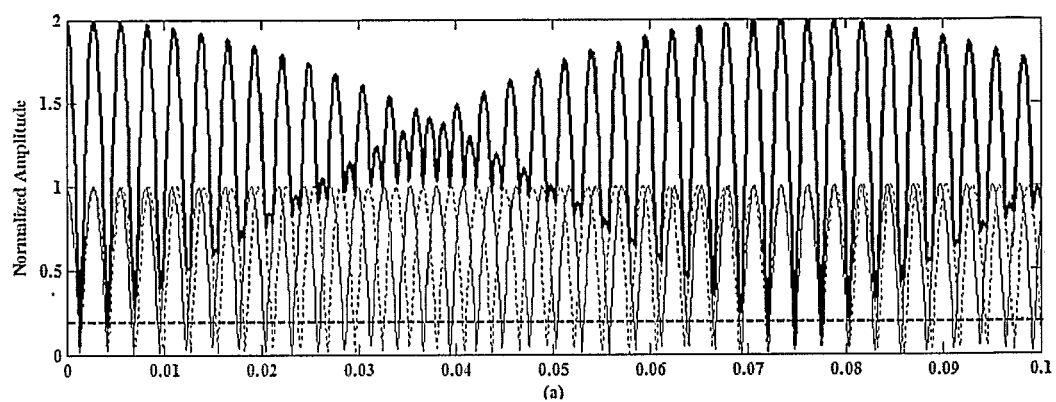
FIGS. 8A-C are exemplary amplitude-versus-distance plots, simulating the operation of a detecting system according to yet another embodiment of the invention.
Figure 8B:
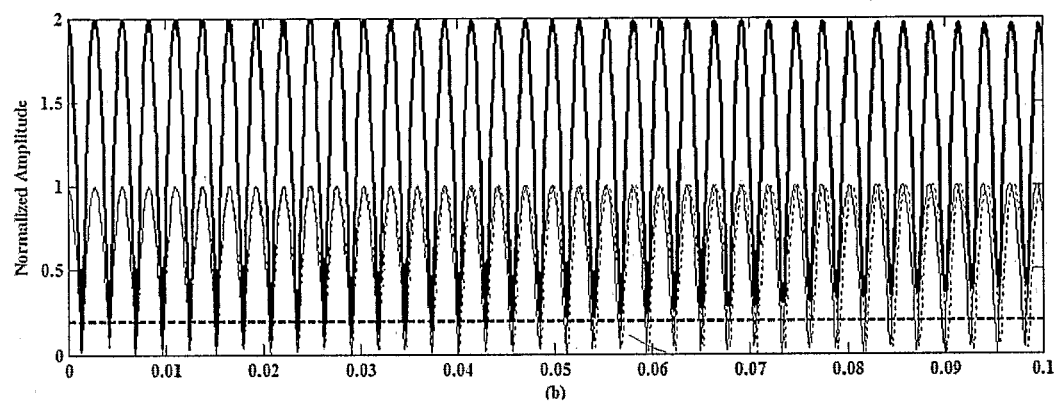
Figure 8C:
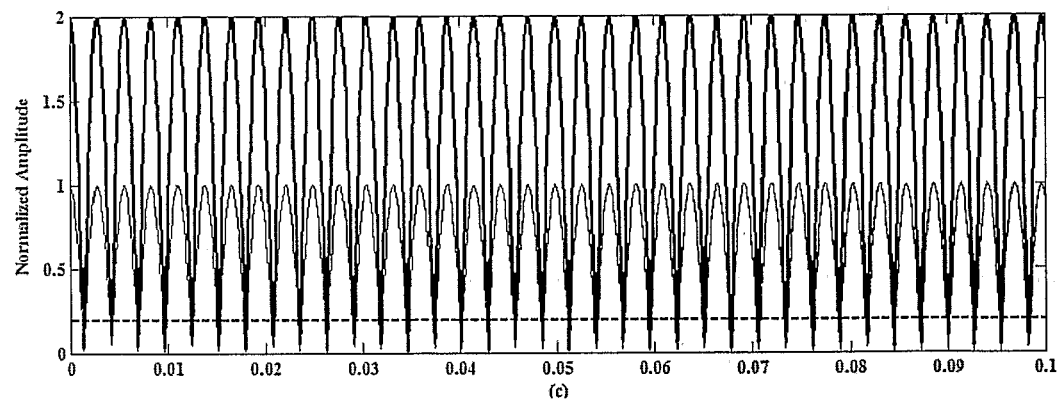

Equations (16) and (17), imply that the lower the frequency $f_1$, the further apart are the resulting null points. Thus the null-point problem is solved at very low $f_1$. However, when the frequency $f_1$ is too small, the null points are very likely to be dominated by the local null points over quite a long distance. FIGS. 8A-C show the different distributions of local null points and global null points for $f_1$=500 MHz, $f_1$=50 MHz, and $f_1$=5 MHz, respectively, when $f_2$=27.1 GHz. The distances are plotted on the horizontal axis, normalized amplitudes of the signals are plotted on the vertical axis. When the signal hits a valley, the amplitude is the smallest and, thus, detection accuracy is the lowest. The light solid and light dotted lines represent the local null points and optimum points distribution for baseband signal components $B_L(t)$ and $B_U(t)$ respectively. The amplitude of $B_L(t)$ and $B_U(t)$ may have a little difference because of frequency response flatness in the transceiver, but here the same amplitude is assumed for convenience of analysis.

From the plot, the nearest local null points (valley) separation is approximately 2.5 mm. The thick solid lines represent the global null points and optimum points distribution for $B(t)$. When $f_1$=500 MHz, the global null points separation is 75 mm, as shown in FIG. 8A. However, for $f_1$=5 MHz, the global null points separation is 7.5 m. As shown in FIG. 8(c), in a whole 0.1 m range, $B(t)$ has the same null points and optimum point as those of $B_L(t)$ and $B_U(t)$, which was qualitatively defined as a global null point previously. Quantitatively, if the signal valley amplitude for $B(t)$ falls under 20% of peak amplitude of either $B_L(t)$ or $B_U(t)$, then we define $B(t)$ as the global null point region. By this definition, $B(t)$ will stay in a global null point region for about 1 m long for $f_1$=5 MHz, 0.1 m for 50 MHz, and 0.01 m for 500 MHz.

To overcome this null point problem in the measurement, and to obtain high detection accuracy, it is better to make the measurement at or near the optimum point by either moving the radar position or changing the $f_1$ frequency. For an LO1 frequency as low as 5 MHz, it is hard to move as much as 3 m distance for the radar to reach a nearest optimum point, so the only way is to adjust the LO1 frequency.

For Ka-band wave, the signal loss over distance is much higher than low frequency wave. For the same power level at receiver, the propagating distance for the Ka-band wave will be much shorter. In this measurement, using low power transmission, the detection accuracy starts to drop quickly when the distance increases to 2.5 m. If a null point occurs at $d_0$=2.5 m, then to switch this null point to an optimum point, the $f_1$ frequency will need to be changed at least 7.5 MHz according to equation (15). If a null point occurs at $d_0$=0.1 m, the smallest tuning step will be 187.5 MHz, which is quite a large tuning range for the first low oscillator (LO1). Therefore, the selection of $f_1$ frequency and the VCO tuning range are considered together when the null point appears at a distance close to the system 100. Therefore, tuning range of the system 100 from 450 MHz to 800 MHz VCO is preferably selected as the $f_1$ source. At the same time, this VCO frequency provides about 75 mm null point separation, so it also provides a possibility to avoid the null point by adjusting the position of the system 100 relative to the target.

When the detection accuracy is very low, one problem is likely to arise: it is likely to be difficult to determine whether the system 100 is detecting a false alarm caused by the null point or, in fact detecting a significant result, such as a warning for the subject being monitored. Under this situation, if the detection accuracy can be increased significantly by either adjusting the position of the system 100 relative to a target or changing frequency f, it means a false alarm due to null point. Otherwise, in the context of patient monitoring, for example, it indicates that the patient may have a cardiopulmonary problem.

As already described, detection accuracy generally depends on a target's position relative to the system, which may be at the null point, the optimum point, or somewhere in between. However, the system 100 is able to attain the optimal response by tuning the frequency $f_1$. Accordingly, the system 100 achieves high detection accuracy regardless of the position of the target relative to the system.

Figure 9:
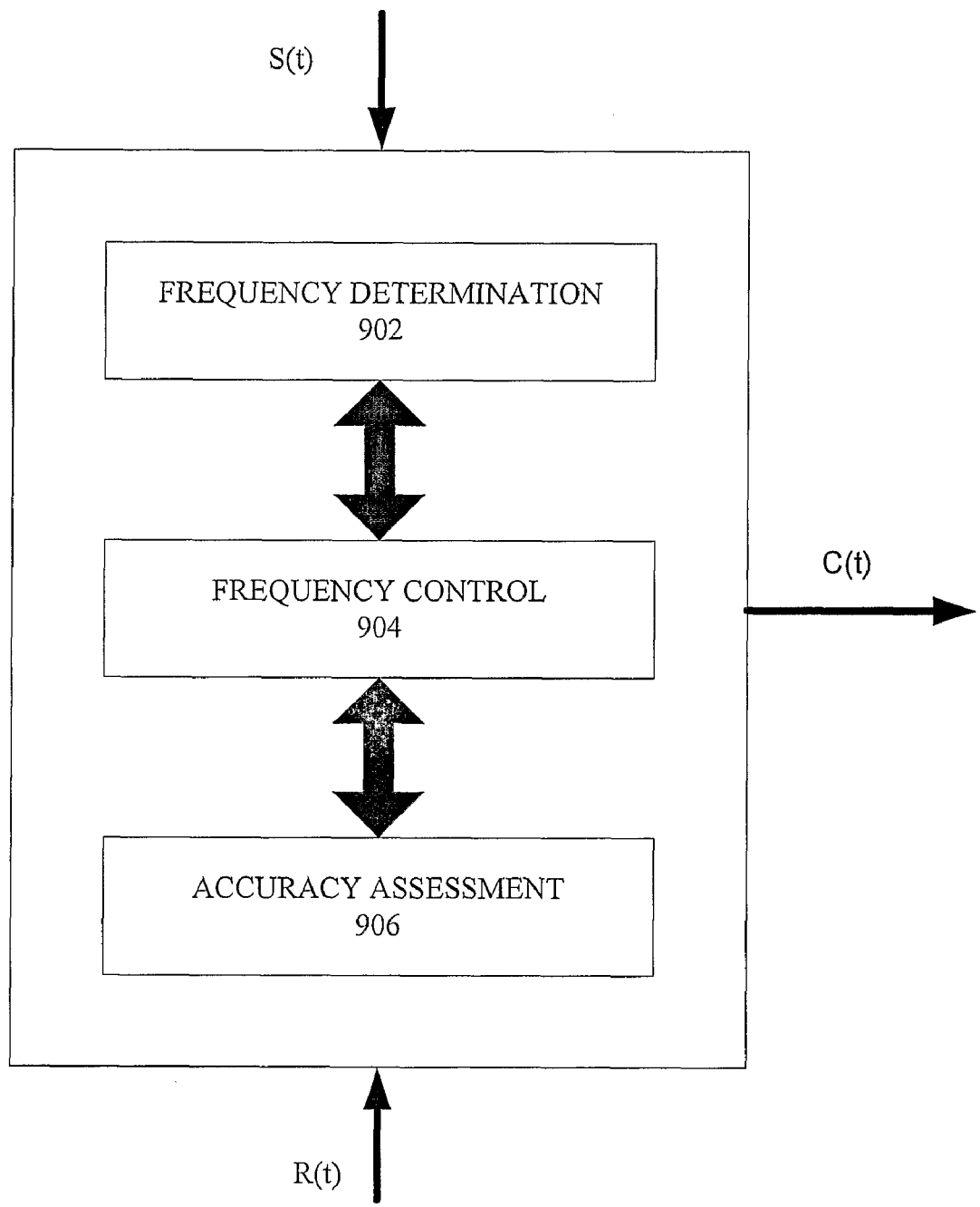
FIG. 9 is a schematic diagram of a frequency separation unit, according to yet another embodiment of the invention.

FIG. 9 is a schematic diagram of a frequency separation unit 900, according to another embodiment of the invention. The frequency separation unit 900 determines a desired separation between a first frequency component $f_1$ and a second frequency component $f_2$ of a double-sideband Ka-band electromagnetic wave used for sensing a target. Illustratively, the frequency separation unit 900 comprises a frequency determining module 902, an accuracy assessment module 904, and frequency control module 906 in communication with one another.

Operatively, the frequency determining module 902 receives a signal S(t) corresponding to the double-sideband Ka-band electromagnetic wave. For example, the double-sideband Ka-band electromagnetic wave can be supplied directly to the module. Alternatively, a signal representative of the physical parameters of the double-sideband Ka-band electromagnetic wave can be supplied. A signal R(t) representative of the detection accuracy of the double-sideband Ka-band electromagnetic wave is supplied to the accuracy assessment module 904, which determines whether an adjustment in the separation of the first and frequency components, $f_1$ and $f_2$, is warranted. If so, the frequency control module 906 provides a control signal C(t) that causes a change in one or both of the frequency components to effect the desired frequency separation that will enhance the sensing accuracy of the double-sideband Ka-band electromagnetic wave, as described above.

More particularly, as already described, the sensing accuracy is significantly increased by adjusting one or both frequency components, $f_1$ and $f_2$, such that the optimum points of a signal response induced by one sideband of the double-sideband Ka-band electromagnetic wave overlap entirely or substantially null points of a signal response induced by the other sideband of the double-sideband Ka-band electromagnetic wave due to the separation between the two frequency components.

It is to be understood that, more generally, but nonetheless consistent with the techniques described herein, detection accuracy is enhanced if a spike in a signal response induced by one side band of the double-sideband Ka-band electromagnetic wave overlaps entirely or substantially a null point of a signal response induced by the other sideband. Again, according to the invention, this can be achieved by adjusting one or both of the frequency components, $f_1$ and $f_2$, so as to obtain a desired separation between the frequency components. As defined herein, a spike is a signal response that exceeds a predetermined threshold.

Each of the exemplary modules of the frequency separation unit 900 can be implemented in hardwired circuitry and/or machine-readable code. Preferably, the frequency separation unit 900 is incorporated into or connected with the previously-described sensing system 100. (See FIG. 1.)

Figure 10:
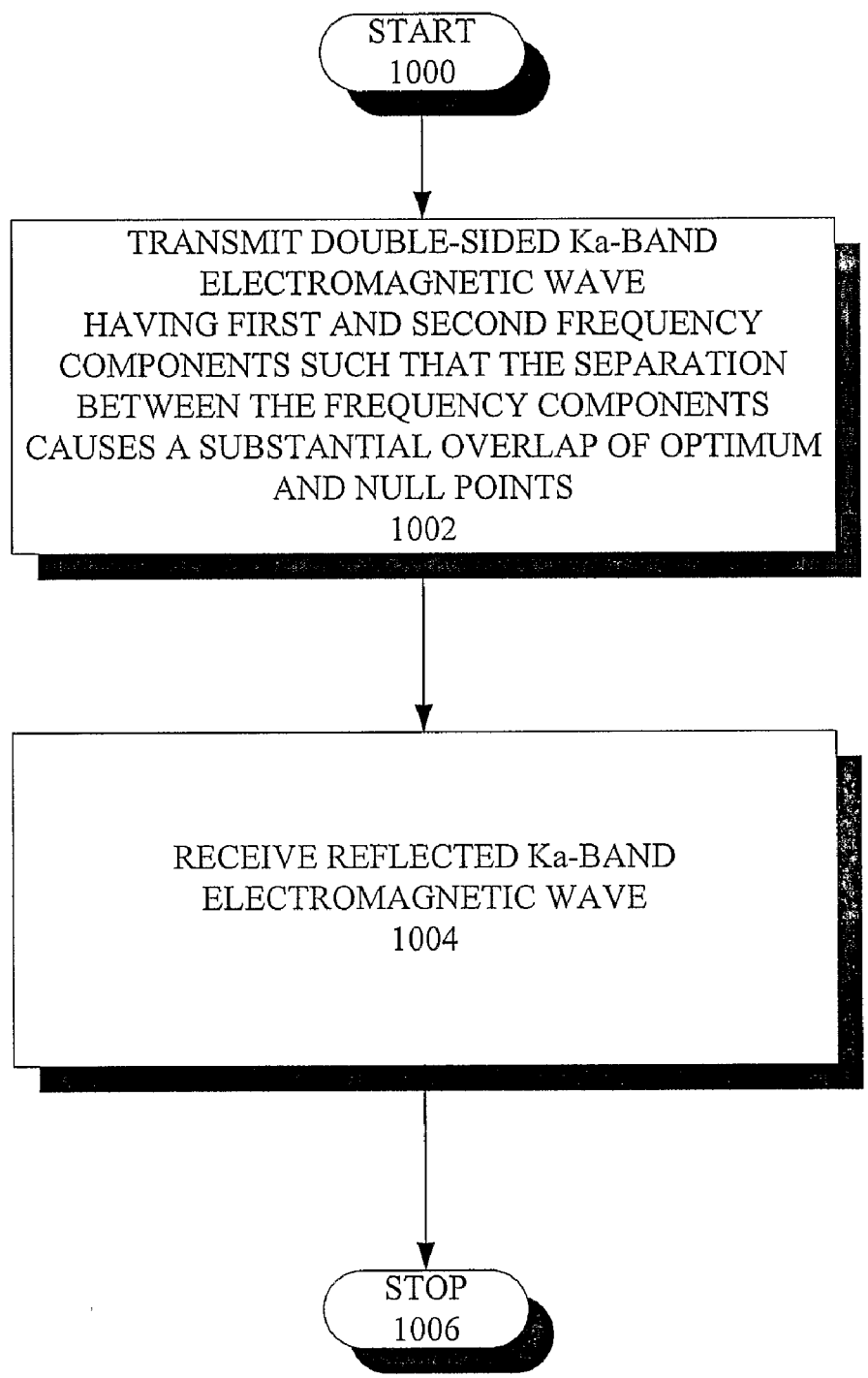
FIG. 10 is a flowchart of the exemplary steps of a method of remotely sensing a target, according to still another embodiment of the invention.

FIG. 10 is a flowchart of the exemplary steps of a method 1000 for remotely sensing a target, according to yet another embodiment of the invention. The method includes, at step 1002, transmitting a double-sided Ka-band electromagnetic wave comprising a first frequency component and a second frequency component. At step 1004, the method 1000 continues with the receiving of the Ka-band electromagnetic wave after it is reflected by a subject. The separation between the first and second frequency components causes each optimum point corresponding to a side band of the double-sided Ka-band signal to substantially overlap each null point corresponding to a different side band of the double-sided Ka-band signal, as already described. The method concludes 1006.

Figure 11:
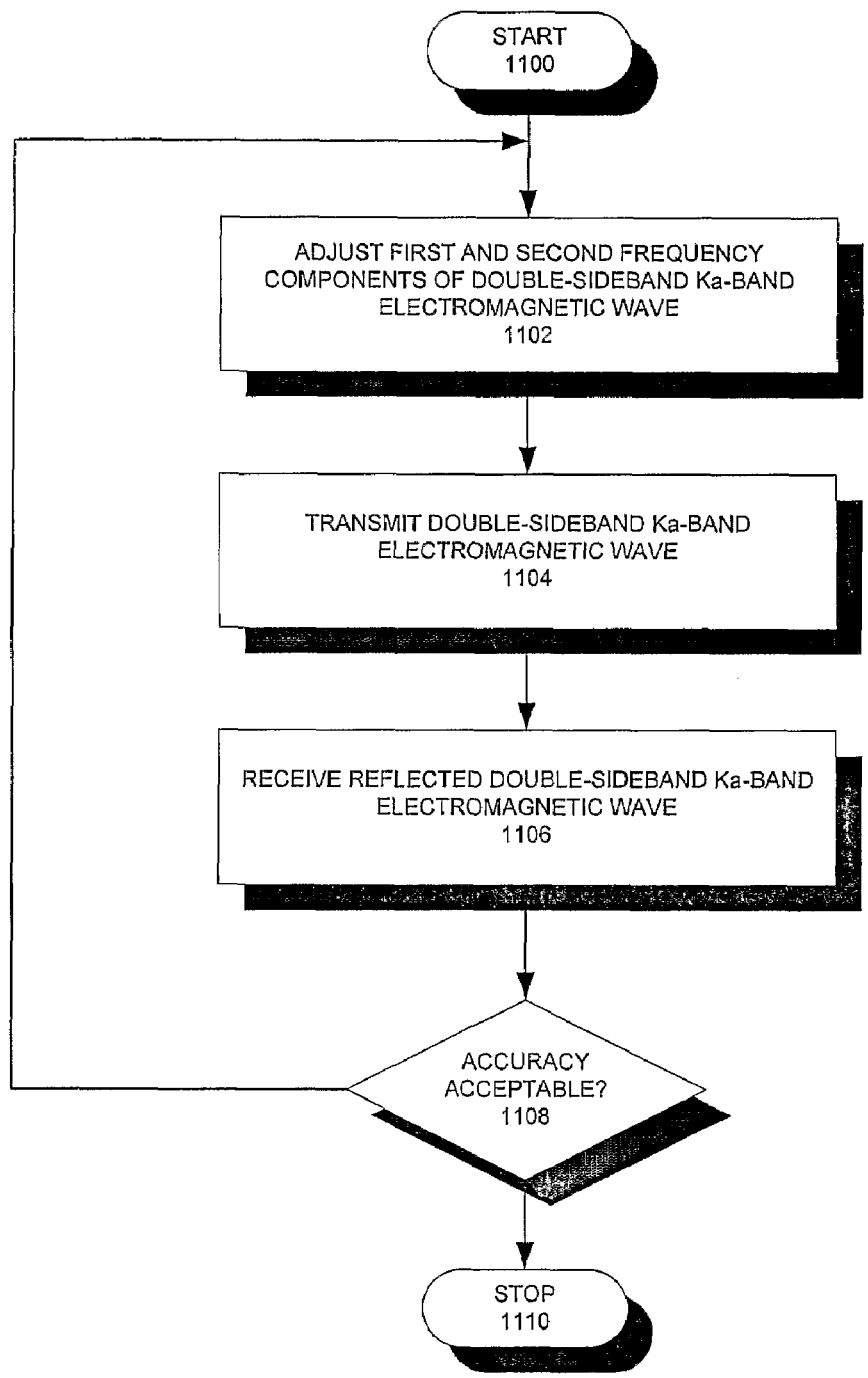
FIG. 11 is a flowchart of the exemplary steps of a method for determining a frequency component separation for a double-sideband Ka-band electromagnetic wave used to remotely sense a target, according to yet another embodiment of the invention.

FIG. 11 is a flowchart of the exemplary steps of a method 1000 for determining a frequency component separation for double-sideband Ka-band electromagnetic wave used to remotely sense a target, according to yet another embodiment of the invention. The method includes at step 1102 adjusting at least one of the first and second frequency components of the double-sideband Ka-band electromagnetic wave. The double-sideband Ka-band electromagnetic wave is transmitted at step 1104. The transmitted wave is reflected and received at step 1106, after which the detection accuracy of the wave is assessed at step 1108. If the detection accuracy is not acceptable according to a predefined threshold or criterion, the preceding steps are repeated until an acceptable accuracy is attained. When an acceptable accuracy is attained, the method concludes at step 1110.

More particularly, according to the method, one or both of the first and second frequencies, $f_1$ and $f_2$, are adjusted so that the separation between the frequencies causes a substantial or complete overlap of the optimum points from one sideband with the null points of the other sideband of the double-sideband Ka-band electromagnetic wave. More generally, as already noted, detection frequency is enhanced when one or both of the frequencies are adjusted so as to effect a separation between the frequencies that causes spikes from one sideband to completely or substantially overlap the null points from the other sideband of the Ka-band electromagnetic wave.

Figure 12:
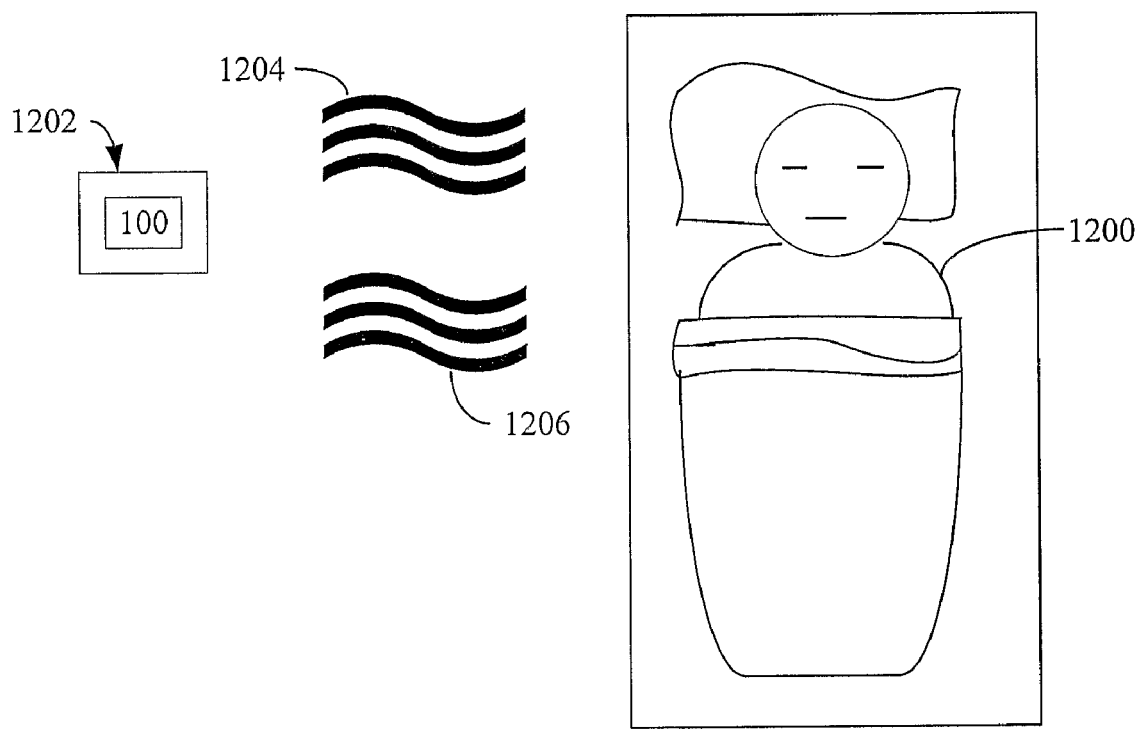
FIG. 12 is a schematic diagram of a baby monitor, according to still another embodiment of the invention.

As already noted, the invention has wide applicability in the health-care field, such as for diagnostics and for monitoring the heartbeat and respiration of a patient or invalid. The invention, however, also encompasses various non-medical applications as well. FIG. 12 schematically illustrates one such application, according to still another embodiment of the invention, that of monitoring the heartbeat or respiration of an infant or young child 1200. As illustrated, the remote sensing system 100, described above, can be incorporated into or connected with a baby monitor 1202. Functioning as a baby monitoring system, the system 100 transmits a signal 1204 to the baby 1200 and receives a reflected signal 1206 from the baby. As also described above, the system 100 accordingly detects the movement of the chest of the baby 1200 so as to monitor the baby's heartbeat.

As will be readily understood by one of ordinary skill in the art, the system 100 can be implemented in an integrated chip and encased in a housing of the baby monitor 1202. (The relative low power used by the system 100 and the shorter wavelengths of the signals in the Ka-band, which permit use of an antenna having a much reduced size relative to conventional devices, are among the reasons that the system can be so implemented.) In alternative embodiments, the system 100 can be installed within a laptop, cellular phone, or other handheld device. The system 100, moreover, can comprise hardware and/or software for converting the transmitted and reflected signals 1204, 1206 into digital form for creating an electrocardiogram-like image on a screen of the laptop, cellular phone, or other handheld device.

According to yet another embodiment, the baby monitor 1200 can include a transmitter (not explicitly shown) connected to the system 100. The transmitter can receive the output of the system 100 and transmit the output to a wireless device remote from the baby monitor 1200. The output of the system 100, for example, can be transmitted to cellular phone or laptop having a screen on which the electrocardiogram-like image or other monitoring information can be displayed. This embodiment affords the advantages of a parent or nurse being able to move about in areas remote from the baby's room, while still being able to closely monitor the baby.

Figure 13:
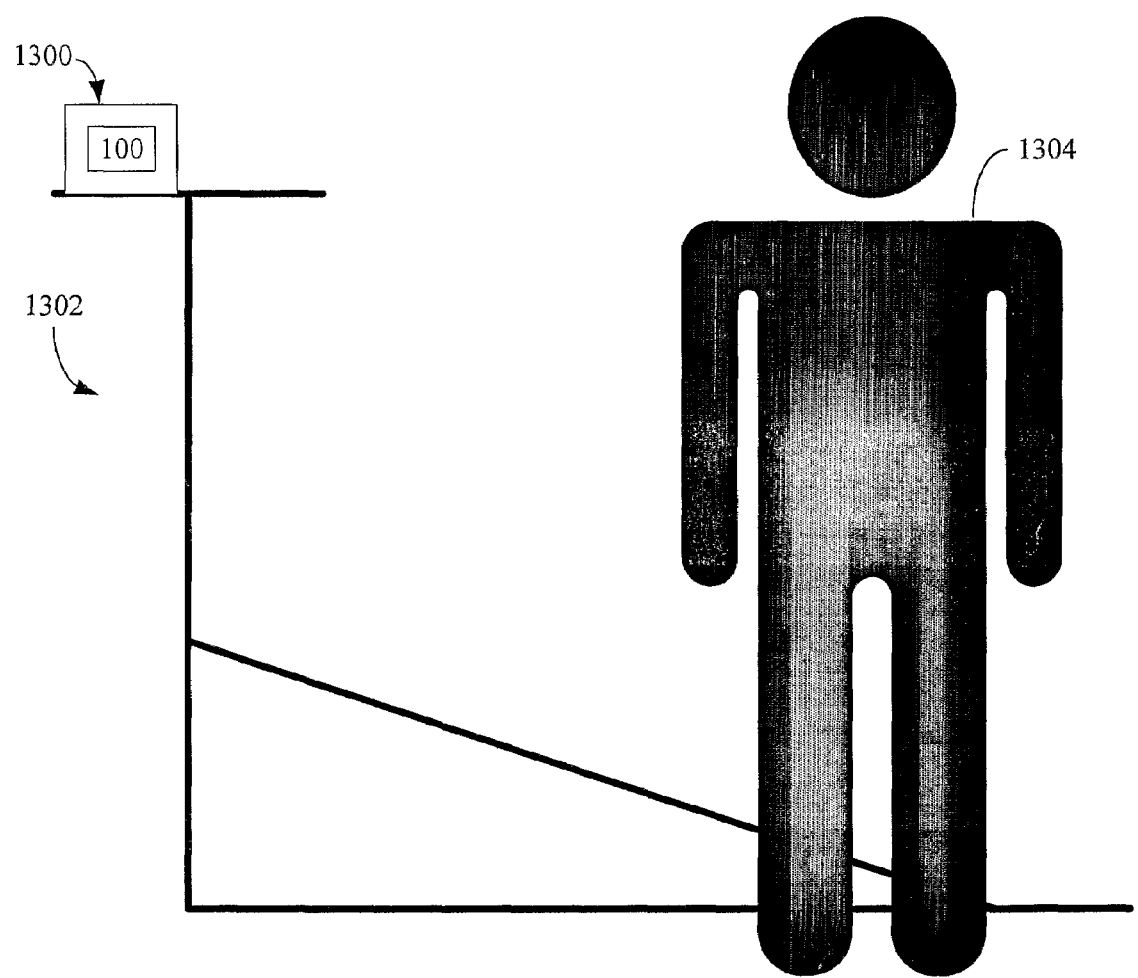
FIG. 13 is a schematic diagram of an exercise monitor, according to yet another embodiment of the invention.

Another non-medical application of the invention is schematically illustrated in FIG. 13, according to yet another embodiment of the invention. According to this embodiment, the system 100 serves as an exercise monitor. The system 100 is illustratively encased in a housing 1300 mounted to or in the vicinity of an exercise device, such as a treadmill 1302. When so positioned in the vicinity of a person 1304 engaged in exercise or resting during an extended exercise regime, the system 100 can monitor the heartbeat and/or respiration of the person. Other embodiments include, for example, monitoring humans located in a medical facility such as a hospital and monitoring animals located in a facility such as a research laboratory.

The invention offers several unique advantages. One advantage is that the Ka-band frequency spectrum tends to be used only sparingly, thus reducing the risk that the system will experience interference from other applications.

Another advantage is that the correspondingly shorter wavelengths of the signals at these frequencies are more sensitive to small displacements. The modulated phase in the baseband output is inversely proportional to the wavelengths. Thus, for the same displacement, the shorter wavelengths generate larger phase modulation. For example, if the system is operated in a frequency range from 26 GHz to 40 GHz, the corresponding wavelengths are from 11.5 mm down to 7.5 mm. Therefore, the phase generated by a 30 GHz wave (with a corresponding wavelength of 10 mm) is 12.5 times, or approximately 22 dB, greater than one at 2.4 GHz (with a corresponding wavelength of 125 mm).

Yet another advantage stems from the shorter wavelengths that can be used in practicing the invention. The shorter wavelengths of signals in the Ka-band, for example, allow for use of an antenna having a much reduced size relative to conventional devices. Indeed, as already noted, the size of the described herein is such that it is small enough to be integrated on a chip.

Some of the particular advantages of practicing the invention using double-sideband signals in the Ka-band have been particularly noted herein. Yet, while the invention has been described herein primarily in the context of using signals in the Ka-band, it will be readily apparent that the invention is not limited in this respect. Indeed, it will be readily apparent that the invention as described herein can be practiced using frequencies above the Ka-band as well. Thus, while there are particular advantages to using double-sideband signals whose frequencies are in the Ka-band, the invention applies to double-sideband signals having frequencies in the Ka-band as well as above the Ka-band.

The invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The invention can be embodied in other forms without departing from the spirit or essential attributes thereof. Accordingly, reference should be made to the following claims, rather than to the foregoing specification, as indicating the scope of the invention.

That claimed is:

1. A method of remote sensing, the method comprising:
   transmitting a double-sideband signal comprising a first frequency component and a second frequency component; and
   receiving the double-sideband signal after it is reflected by a subject;
   wherein a separation between a first frequency of the first frequency component and a second frequency of the second frequency components causes a spike in a signal response corresponding to one sideband of the received double-sideband signal to substantially overlap a null point of a signal response corresponding to the other sideband of the received double-sideband signal.

2. The method of claim 1, wherein the spike is an optimum point.

3. The method of claim 1, further comprising determining a separation between the first frequency and the second frequency that causes the spike to substantially overlap the null point.

4. The method of claim 1, further comprising adjusting at least one of the first frequency and the second frequency to thereby effect the separation that causes the spike to substantially overlap the null point.

5. The method of claim 4, wherein adjusting the at least one of the first frequency and the second frequency to thereby effect the separation comprises sampling a plurality of detection sensitivity measurements, each of the plurality of detection sensitivity measurements corresponding to a different separation between the first frequency and the second frequency, and selecting from among the different separations a separation corresponding to a greatest detection sensitivity from the plurality of detection sensitivity measurements.

6. The method of claim 1, further comprising generating the double-sideband signal by multiplying a first signal having a frequency equal to the first frequency and a second signal having a frequency equal to the second frequency.

7. The method of claim 1, wherein the first frequency and the second frequency are within a Ka-band of an electromagnetic spectrum.

8. A sensing system, comprising:
   a transceiver including
      a transmitter chain that transmits a double-sideband signal having a first frequency component and a second frequency component, and
      a receiving chain that receives the double-sideband signal after it is reflected by a target; and
   a baseband circuit for extracting information content from the received double sideband signal;
   wherein a separation between a first frequency of the first frequency component and a second frequency of the second frequency component causes a spike in a signal response generated by one sideband of the received double-sideband signal to substantially overlap a null point of a signal response generated by the other sideband of the received double-sideband signal.

9. The system as in claim 8, wherein the spike is an optimum point.

10. The system as in claim 8, wherein the receiving chain is configured according to a two-step indirect conversion receiver architecture.

11. The system as in claim 8, wherein the target is a monitored patient.

12. The system as in claim 8, further comprising a frequency determining unit.

13. The system of claim 12, wherein the frequency determining unit comprises at least one of a frequency determining module, an accuracy assessment module, and a frequency control module.

14. The system of claim 8, wherein the system comprises a baby monitor.

15. The system of claim 8, wherein the system comprises an exercise monitor for monitoring an individual engaged in an exercise regimen.

16. A machine-readable storage medium, the storage medium comprising machine-directing instructions for:
   transmitting a double-sideband signal comprising a first frequency component and a second frequency component; and
   receiving the double-sideband signal after it is reflected by a subject;
   wherein a separation between a first frequency of the first frequency component and a second frequency of the second frequency components causes a spike in a signal response corresponding to one sideband of the received double-sideband signal to substantially overlap a null point of a signal response corresponding to the other sideband of the received double-sideband signal.

17. The storage medium of claim 16, wherein the spike is an optimum point.

18. The storage medium of claim 16, further comprising a machine-directing instruction for adjusting at least one of the first frequency and the second frequency to thereby effect the separation that causes the spike to substantially overlap the null point.

19. The storage medium of claim 16, further comprising a machine-directing instruction for determining the separation between the first frequency and the second frequency that causes the spike to substantially overlap the null point.

20. The storage medium of claim 19, wherein the machine-directing instruction for determining the separation comprises an instruction for sampling a plurality of detection sensitivity measurements, each detection sensitivity measurement corresponding to a different separation between the first frequency and the second frequency, and selecting from among the different separations a separation corresponding to a greatest detection sensitivity from the plurality of detection sensitivity measurements.

21. The storage medium of claim 16, further comprising a machine-directing instruction for generating the double-sideband signal by multiplying a first signal having a frequency equal to the first frequency component and a second signal having a different frequency equal to the second frequency.

22. The method according to claim 1, wherein the subject is a monitored patient.

23. The method according to claim 1, wherein the subject is an individual engaged in an exercise regimen.

24. The method according to claim 1, further comprising:
down converting the received double-sideband signal into a baseband signal being a superposition of a first baseband signal component corresponding to the first frequency component and a second baseband signal component corresponding to the second frequency component,
wherein the respective amplitudes of the first baseband signal component and the second baseband signal component vary between a minimum and a maximum with a distance between a transmitter for transmitting the double-sideband signal and the subject.

25. The method according to claim 24, further comprising:
adjusting the separation between the first frequency and the second frequency by adjusting at least one of the first frequency and the second frequency until, after the double-sideband signal is reflected by the subject, received, and down converted, the first baseband signal component and the second baseband signal component are in quadrature, such that the minimum amplitude of the first baseband signal component and the maximum amplitude of the second baseband signal component occur respectively at the same distance, and vice versa.

26. The system according to claim 8, wherein the first frequency is within a Ka-band, wherein the second frequency is within the Ka-band.

27. The system according to claim 8, wherein the baseband circuit down converts the received double-sideband signal into a baseband signal, and outputs an output signal indicative of a movement of the target.

28. The system according to claim 27, wherein the movement is breathing by the target.

29. The system according to claim 27, wherein the movement is the target's heart beating, such that the output signal is indicative of heart rate.

30. The system according to claim 27, wherein the baseband signal is a superposition of a first baseband signal component corresponding to the first frequency component and a second baseband signal component corresponding to the second frequency component, wherein the respective amplitudes of the first baseband signal component and the second baseband signal component vary between a minimum and a maximum with a distance between the transceiver and the target.

31. The system according to claim 30, further comprising a frequency separation unit connected to the transceiver and adapted for adjusting the separation by adjusting at least one of the first frequency and the second frequency until, after the double-sideband signal is reflected by the subject, received, and down converted, the first baseband signal component and the second baseband signal component are in quadrature, such that the minimum amplitude of the first baseband signal component and the maximum amplitude of the second baseband signal component occur respectively at the same distance between the transceiver and the target, and vice versa.

32. The method according to claim 1, further comprising:
outputting an output signal indicative of a movement of the subject.

33. The method according to claim 32, wherein the output signal is indicative of the subject's respiration rate.

34. The method according to claim 32, wherein the output signal is indicative of the subject's heart rate.

* * * * *

UNITED STATES PATENT AND TRADEMARK OFFICE
CERTIFICATE OF CORRECTION

Page 1 of 1

PATENT NO. : 7,903,020 B2
APPLICATION NO. : 11/911716
DATED : March 8, 2011
INVENTOR(S) : Jenshan Lin and Yanming Xiao It is certified that error appears in the above-identified patent and that said Letters Patent is hereby corrected as shown below:

Column 3,
Line 28, "of the is a system" should read --of the invention is a system--.

Column 5,
Lines 13-14, "can implemented" should read --can be implemented--.
Line 22, "Ka-hand" should read --Ka-band--.

Column 9,
Line 53, "θhd L" should read --$\theta_L$--.

Column 16,
Line 38, "second frequency components" should read --second frequency component--.

Signed and Sealed this
Seventeenth Day of May, 2011

David J. Kappos
*Director of the United States Patent and Trademark Office*